United States Patent [19]
Oishi et al.

[11] Patent Number: 4,808,189
[45] Date of Patent: Feb. 28, 1989

[54] POWDERED HAIR DYE CONTAINING CYCLODEXTRIN INCLUSION COMPLEX

[75] Inventors: Takeshi Oishi, Seto; Fumio Nakanishi, Tajimi; Toshihiko Yamamoto, Toyohashi, all of Japan

[73] Assignee: Hoyu Co., Ltd., Japan

[21] Appl. No.: 86,808

[22] Filed: Aug. 19, 1987

[30] Foreign Application Priority Data

Feb. 4, 1987 [JP] Japan .................................. 62-24171

[51] Int. Cl.$^4$ ................................................ A61K 7/13
[52] U.S. Cl. ........................................... 8/408; 8/406; 8/409; 8/410; 8/411; 8/412
[58] Field of Search ................... 8/405, 406, 408, 409, 8/410, 411, 412

[56] References Cited

U.S. PATENT DOCUMENTS

| 4,402,698 | 9/1983 | Kalopissis et al. | 8/406 |
| 4,548,811 | 10/1985 | Kubo et al. | 424/71 |
| 4,629,466 | 12/1986 | Rose et al. | 8/408 |
| 4,678,598 | 7/1987 | Ogino et al. | 252/DIG. 14 |

FOREIGN PATENT DOCUMENTS 148043 12/1976 Japan .
18606 1/1982 Japan .

OTHER PUBLICATIONS

WPI Acc No. 80-082170/05; Abstract for JP54158941 (12/1979).
WPI Acc No. 85-239959/39; Abstract for JP60156761 (8/1985).
WPI Acc No. 85-281017/45; Abstract for JP60192729 (10/1985).
WPI Acc No. 87-027032/04; Abstract for JP61285403 (12/1986).
WPI Acc No. 87-082332/12; Abstract for JP62032082 (2/12/87).
WPI Acc No. 87-166374/24; Abstract for JP62097881 (5/7/87).
WPI Acc No. 87-167588/24; Abstract for JP62100557 (5/11/87).
"Cyclodextrin Chemistry", Bender et al., Reactivity and Structure Concepts in Organic Chemistry, vol. 6.

Primary Examiner—Paul Lieberman
Assistant Examiner—Linda D. Skaling
Attorney, Agent, or Firm—Parkhurst, Oliff & Berridge

[57] ABSTRACT

A powdered hair dye includes a dye component included in cyclodextrin. Because of the complex formation, it possesses high stability for longer shelf life, color-fastness and deeper color: and maintains hair in good condition. Because of the powder, it is easy for the manufacturer to control manufacturing and transport. As for the users, it is light weight, easily carried and economical.

4 Claims, No Drawings

POWDERED HAIR DYE CONTAINING CYCLODEXTRIN INCLUSION COMPLEX

BACKGROUND OF THE INVENTION

This invention relates to a powdered hair dye, and more particularly to a powdered hair dye which can dye a deep color with an advantage of possessing high stability for longer shelf life.

Because the powdered hair dye has many advantages compared with the liquid type, and it would become more widely used in the future. For the users, the powdered type is light weight, easily carried and economical because it is simple to apportion. For the manufacturer, it is easy to control manufacturing and transport.

Two types of powdered hair dyes are generally known. One is a so-called one-component type, that is, a mixture of a powdered oxidation dye and a powdered oxidizing agent packaged together. The other is a so-called two-component type, that is, a powdered oxidation dye and a powdered oxidizing agent separately packaged. The two-component type of which only the oxidation dye is powdered is also available. In any case, the oxidation dye and the oxidizing agent of the powdered hair dyes are mixed just prior to their use to prepare a tinting mixture. Thus, each component of the hair dye has to be stably stored without deterioration until being prepared as the tinting mixture.

When the oxidation dye or a dye component is stored in a powdery state for a long time, however, it tends to be deteriorated by the effects of moisture. Especially, the tendency is remarkable if the dye component includes both a primary intermediate and a coupler. Furthermore, in the one-component type, since the oxidizing agent acts on the dye components during storage, they are apt to be deteriorated.

Even a part of the dye component is deteriorated during storage, it is hard to achieve a desired and fast color.

SUMMARY OF THE INVENTION

This invention has been made in order to prevent the above-described problems from the powdered hair dye.

It is an object of this invention to provide a powdered hair dye which possesses high stability for longer shelf life.

It is another object of this invention to provide a powdered hair dye which dyes hair a deep color.

It is a further object of this invention to provide a powdered hair dye of fast color.

The above objects and other related objects are realized by a powdered hair dye of this invention which includes a dye component or its salt as an inclusion complex.

Accordingly, because of the complex formation, the effects as above can be obtained. Furthermore, because of the powder, it is easy for the manufacturer to control manufacturing and transport. As for the users, it is light weight, easily carried and economical.

DISCLOSURE OF THE INVENTION

This invention is now explained in detail.

As a dye component of this invention, a primary intermediate, a coupler or a nitro dye component can be employed which are normally known as a hair dye component. The primary intermediate is exemplified as p-phenylenediamine, o-phenylenediamine, p-aminodiphenylamine, p-aminophenol, o-aminophenol, toluene-2,5-diamine, toluene-3,4-diamine, 4,4'-diaminodiphenylamine, p-methylaminophenol, p-chloro-o-phenylenediamine, o-chloro-p-phenylenediamine, 5-amino-o-cresol, 3,3'-iminodiphenol, 2,6-diaminopyridine, p-aminophenylsulfamic acid, 2,4-diaminophenol or 2,4-diaminoanisole. The coupler is, for example, m-phenylenediamine, toluene-2,4-diamine, m-aminophenol, p-methoxy-m-phenylenediamine, α-naphthol, resorcinol, hydroquinone, catechol, 4-chlororesorcinol, pyrogallol or fluoroglycine. The nitro dye is, for example, nitro-p-phenylenediamine, p-nitro-o-phenylenediamine, 2-amino-4-nitrophenol, 2-amino-5-nitrophenol, 4-amino-2-nitrophenol, picramic acid, picric acid, 1,2-diamino-4-nitrobenzene, 2-nitro-p-toluylenediamine or 1,4-diaminoanthraquinone. The above dye component may be used as a salt of organic acid or a salt of inorganic acid such as sulfate, hydrochloride and acetate. The above dye component may also be used one or a combination of two or more of the compounds listed above. The amount of the dye component used is usually 0.01 to 40 parts in 100 parts of the whole hair dye. Here and hereinafter, the part is a weight part.

The powdered hair dye of this invention includes the above one or more dye components as an inclusion complex with, for example, cyclodextrin. The cyclodextrins are a series of oligosaccharides produced by the action of the amylase of Bacillus macerans on starch and related compounds. Cyclodextrins are composed of α-(1,4)-linkages of a number of D(+)-glucopyranose units. Cyclodextrins are designated by a Greek letter to denote the number of glucose units: α-for 6, β-for 7, γ-for 8 and so on. The molar ratio of cyclodextrin:the dye component is usuallyin the range of 1:0.1 to 1:3 in the preparation. If the ratio of cyclodextrin is too low, the dye component is not sufficiently included. Thus such a powdered hair dye is in lack of high stability of shelf life. On the contrary, if the ratio of cyclodextrin is too high, it becomes uneconomical because the effect can not be enhanced by the high ratio.

The dye component can be included in the cyclodextrin cavity by a general method. The inclusion complex must be easily dissolved when the tinting mixture is prepared. Cyclodextrin does not have an adverse effect on human body. When two or more compounds are employed as the dye component, they may be included together. The amount of the inclusion complexes is usually 0.05 to 50 parts in 100 parts of the whole hair dye, and preferably 0.1 to 40 parts.

The oxidizing agent may be packaged separately. But usually it is preferably that the hair dye is one-component type which the inclusion complex and the oxidizing agent are mixed and packed together. In this case, of course, it is necessary to employ a powdered oxidizing agent such as sodium perborate, potassium perborate, urea peroxide, sodium percarbonate, malemaine peroxide, sodium sulfate.hydrogen peroxide adduct, sodium pyrophosphate.hydrogen peroxide adduct and disodium phosphate.hydrogen peroxide adduct. In the case of the two-component type of which only the oxidizing agent is liquid, hydrogen peroxide can be employed.

To the hair dye of this invention, various additives which are included in prior art hair dyes can be added. In order to apply a hair dye easily on hair, appropriate amount of a thickener, a surface active agent, an inorganic compound, an organic acid, an alkalizing agent, a perfume or a conditioning component may be added as occasion demands. The thickener is starch, seaweed, sodium alginate, methylcellulose, hydroxyethylcellulose, carboxymethylcellulose, polyvinyl alcohol, polyvinylpyrrolidone or sodium polyacrylate. The surface active agent is higher alkylbenzene sulfonate, fatty acid soap, higher alkyl sulfonate and higher alkylphosphonic ester. The inorganic compound is ammonium nitrate, ammonium carbonate, ammonium chloride, ammonium dihydrogenphosphate, diammonium hydrogenphosphate, or ammonium sulfate. The organic acid is citric acid, tartaric acid, lactic acid or succinic acid. The alkalizing agent is sodium carbonate or sodium silicate.

To use the powdered hair dye of this invention, the dye component with the oxidizing agent are dissolved in a liquid reagent to make its concentration within the range of between 8 and 25 weight % so as to prepare a creamy consistency tinting mixture. It is applied on hair with a comb, a brush or hands.

EXAMPLE

Examples of this invention are as follows. Since there may be many modifications without departing from the scope of the invention, the examples below are not intended to limit the invention to the examples but to illustrate the invention more clearly.

EXAMPLE 1

Each dye of a weight listed below is included in 350 g of cyclodextrin (hereinafter refered to CD) so as to obtain each powdered inclusion complex.

| | |
|---|---|
| p-phenylenediamine | 10 g |
| m-aminophenol | 10 g |
| m-phenylenediamine hydrochloride | 20 g |
| resorcinol | 10 g |

Using the obtained inclusion complexes, a powdered hair dye composition listed below is prepared.

| | | |
|---|---|---|
| CD-p-phenylenediamine complex | | 40 parts |
| (dye component | 1.11 parts) |
| CD-m-aminophenol complex | | 10 parts |
| (dye component | 0.28 parts) |
| CD-m-phenylenediaminehydrochloridecomplex | | 5 parts |
| (dye component | 0.27 parts) |
| CD-resorcinol complex | | 5 parts |
| (dye component | 0.14 parts) |
| sodium pyrophosphate.hydrogen peroxide adduct | | 15 parts |
| carboxymethylcellulose | | 17 parts |
| sodium laurylsulfate | | 7.8 parts |
| perfume | | 0.2 parts |
| (sum | 100 parts) |

The above powdered hair dye of 20 g is dissolved in 100 ml of water to prepare a tinting mixture. It is applied on gray hair and left in contact with the hair dye for half an hour. Then the hair is shampooed and dried. The hair is dyed like natural-looking black.

The results evaluating color, quality and fastness of the above dyed hair are shown in Table 1. The results evaluating the same points in the accelerated test at 40° C. for six months are shown in Table 2.

EXAMPLE 2

Each dye component of a weight listed below is included in 350 g of CD so as to obtain each powdered inclusion complex.

| | |
|---|---|
| p-toluylenediamine | 15 g |
| m-aminophenol | 10 g |
| resorcinol | 10 g |

Using the obtained inclusion complexes, a powdered hair dye composition listed below is prepared.

| | | |
|---|---|---|
| CD-p-toluylene diamine complex | | 30 parts |
| (dye component | 1.23 parts) |
| CD-m-aminophenol complex | | 4 parts |
| (dye component | 0.11 parts) |
| CD-resorcinol complex | | 2 parts |
| (dye component | 0.06 parts) |
| melamin peroxide | | 30 parts |
| carboxymethylcellulose | | 15 parts |
| ammonium carbonate | | 6 parts |
| sodium carbonate | | 5 parts |
| sodium laurylsulfate | | 7.8 parts |
| perfume | | 0.2 parts |
| (sum | 100 parts) |

Using the above powdered hair dye, the same dyeing as the EXAMPLE 1 is performed. As the result, the hair is dyed bright and natural-looking maroon. The results evaluated from the same test as the EXAMPLE 1 are shown in Tables 1 and 2.

EXAMPLE 3

Using inclusion complexes obtained in EXAMPLE 1, a powdered hair dye composition listed below is prepared.

| | | |
|---|---|---|
| CD-p-phenylenediamine complex | | 35 parts |
| (dye component | 0.97 parts) |
| CD-m-aminophenol complex | | 15 parts |
| (dye component | 0.42 parts) |
| CD-m-phenylenediamine hydrochloride complex | | 5 parts |
| (dye component | 0.27 parts) |
| CD-resorcinol complex | | 5 parts |
| (dye component | 0.14 parts) |
| sodium sulfate.hydrogen peroxide adduct | | 20 parts |
| sodium alginate | | 5 parts |
| ammonium chloride | | 5 parts |
| ammonium silicate | | 5 parts |
| sodium laurylsulfate | | 4.8 parts |
| perfume | | 0.2 parts |
| (sum | 100 parts) |

Using the above powdered hair dye, the same dyeing as the EXAMPLE 1 is performed. As the result, the hair is dyed deep brown. The color is not faded to give reddish tone different from prior art hair dyes. The results evaluated from the same test as the EXAMPLE 1 are shown in Tables 1 and 2.

COMPARATIVE EXAMPLE 1

Each dye component is not included in CD. We made the preparation of the same amount as the EXAMPLE 1. Tables 1 and 2 show the results in the case of using the components as follows:

| | |
|---|---|
| p-phenylenediamine | 1.11 parts |
| m-aminophenol | 0.28 parts |
| m-phenylenediamine hydrochloride | 0.27 parts |
| resorcinol | 0.14 parts |

The amounts of other components (the sum is 41.80 parts) are the same as the EXAMPLE 1. The obtained powdered hair dye of 8.36 g is dissolved in 100 ml of water so as to be the same concentration as the EXAM- PLE 1 and the same operation as the EXAMPLE 1 is performed.

COMPARATIVE EXAMPLE 2

Each dye component is not included in CD. We made the preparation of the same amount as the EXAMPLE 2. Tables 1 and 2 show the results in the case of using the components as follows:

| | |
|---|---|
| p-toluylenediamine | 1.23 parts |
| m-aminophenol | 0.11 parts |
| resorcinol | 0.06 parts |

The amounts of other components (the sum is 65.40 parts) are the same as the EXAMPLE 2. The obtained powdered hair dye of 13.08 g is dissolved in 100 ml of water so as to be the same concentration as the EXAMPLE 2 and the same operation as the EXAMPLE 2 is performed.

COMPARATIVE EXAMPLE 3

Each dye component is not included in CD. We made this preparation of the same amount as the EXAMPLE 3. Tables 1 and 2 show the results in the case of using the components as follows:

| | |
|---|---|
| p-phenylenediamine | 0.97 parts |
| m-aminophenol | 0.42 parts |
| m-phenylenediamine hydrochloride | 0.27 parts |
| resorcinol | 0.14 parts |

The amounts of other components (the sum is 41.80 parts) are the same as the EXAMPLE 3. The obtained powdered hair dye of 8.36 g is dissolved in 100 ml of water so as to be the same concentration as the EXAMPLE 3 and the same operation as the EXAMPLE 3 is performed.

EVALUATING METHOD (1) color

Twenty panellers evaluated. The largest number of evaluation among the following three is shown in Tables 1 and 2.

o: dye, a rich and deep color
Δ: dye, slightly inferior to a rich and deep color
x: dye, inferior to a rich and deep color (2) fastness
(I) shampoo resistance A treatment, in which the dyed hair is washed twice by a regular shampoo on the market and dried, is repeated thirty times. In comparison with hair that is not treated as above, the panellers evaluate as follows:

o: superior
Δ: slightly inferior
x: inferior (II) light resistance

The dyed hair is exposed to the sun for sixty days (amount of solar radiation is 27,000 cal/cm$^2$). In comparison with hair that is not treated as above, the panellers evaluate similar to the above (I).

(3) quality of hair

Twenty panellers evaluated. The largest number of evaluation among the following three is shown in Tables 1 and 2.

o: flexible and easy to comb
Δ: a little inflexible and hard to comb
x: inflexible and hard to comb

What is claimed is:

1. A powdered hair dye comprising in admixture an oxidative dye component and an amount of a powdered oxidizing agent, effective to react with said dye component, wherein said dye component is present in the form of a cyclodextrin inclusion complex, the aount of the dye is from 0.05 to 50 parts in 100 parts of the powdered hair dye and the molar ratio of cyclodextrin:dye is 1:0.1 to 1:3.

2. The powdered hair dye according to claim 1, wherein the dye component comprises
    a primary intermediate selected from the group consisting of p-phenylenediamine, o-phenylenediamine, p-aminodiphenylamine, p-aminophenol, o-aminophenol, toluene-2,5-diamine, toluene-3,4-diamine, 4,4'-diaminodiphenylamine, p-methylaminophenol, p-chloro-o-phenylenediamine, o-chloro-p-phenylenediamine, 5-amino-o-cresol, 3,3'-iminodiphenol, 2,6-diaminopyridine, p-aminophenylsul-

TABLE 1

| | | (RIGHT AFTER PREPARING) | | | |
|---|---|---|---|---|---|
| | | | | FASTNESS | |
| | | COLOR | QUALITY OF HAIR | SHAMPOO RESISTANCE | LIGHT RESISTANCE |
| THIS INVENTION | EX1 | o | o | o | o |
| | EX2 | o | o | o | o |
| | EX3 | o | o | o | o |
| COMPARATIVE EXAMPLE | CE1 | o | x | o | o |
| | CE2 | o | x | o | o |
| | CE3 | o | x | o | o |

TABLE 2

| | | (AFTER ACCELERATED TEST AT 40° C. FOR 6 MONTHS) | | | |
|---|---|---|---|---|---|
| | | | | FASTNESS | |
| | | COLOR | QUALITY OF HAIR | SHAMPOO RESISTANCE | LIGHT RESISTANCE |
| THIS INVENTION | EX1 | o | o | o | o |
| | EX2 | o | o | o | o |
| | EX3 | o | o | o | o |
| COMPARATIVE EXAMPLE | CE1 | x | x | x | x |
| | CE2 | x | x | x | x |
| | CE3 | x | x | x | x | famic acid, 2,4-diaminophenol, 2,4-diaminoanisole and salts thereof; and a coupler selected from the group consisting of m-phenylenediamine, toluene-2,4-diamine, m-aminophenol, p-methoxy-m-phenylenediamine, -naphthol, resorcinol, hydroquinone, catechol, 4-chlororesorcinol, pyrogallol, fluoroglycine and salts thereof.

3. The powdered hair dye according to claim 2, wherein the dye component is a salt of a sulfate, hydrochloride or acetate.

4. The powdered hair dye according to claim 1, wherein the powdered oxidizing agent is at least one material selected from the group consisting of sodium perborate, potassium perborate, urea peroxide, sodium percarbonate, melamine peroxide, sodium sulfate.hydrogen peroxide adduct, sodium pyrophosphate.hydrogen peroxide adduct and disodium phosphate.hydrogen peroxide adduct.

* * * * *